United States Patent
Lee et al.

(10) Patent No.: US 11,918,513 B2
(45) Date of Patent: Mar. 5, 2024

(54) DRAINAGE DEVICES HAVING SELF-CLEARING AND FLOW RESISTANCE CONTROL CAPABILITIES, AND MICROACTUATORS FOR USE THEREWITH

(71) Applicant: Purdue Research Foundation, West Lafayette, IN (US)

(72) Inventors: Hyowon Lee, West Lafayette, IN (US); Simon John, Bar Harbor, ME (US); Hyunsu Park, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 1077 days.

(21) Appl. No.: 16/376,288

(22) Filed: Apr. 5, 2019

(65) Prior Publication Data

US 2019/0307608 A1 Oct. 10, 2019

Related U.S. Application Data

(60) Provisional application No. 62/653,904, filed on Apr. 6, 2018.

(51) Int. Cl.
*A61F 9/007* (2006.01)
*A61F 9/00* (2006.01)
*F16K 99/00* (2006.01)

(52) U.S. Cl.
CPC ........ *A61F 9/00781* (2013.01); *A61F 9/0017* (2013.01); *A61F 9/00736* (2013.01); *F16K 99/0003* (2013.01); *F16K 2099/0088* (2013.01)

(58) Field of Classification Search
CPC ................ A61F 9/00781; A61F 9/0017; A61F 9/00736; F16K 99/0003; F16K 99/0034; F16K 2099/0088; A61M 2025/0019; A61M 27/006; B08B 9/027
See application file for complete search history.

(56) References Cited

U.S. PATENT DOCUMENTS

| | | | | |
|---|---|---|---|---|
| 5,945,898 A | * | 8/1999 | Judy | G02B 26/0841 335/78 |
| 10,058,685 B2 | * | 8/2018 | Samoocha | B08B 9/027 |
| 2008/0281250 A1 | * | 11/2008 | Bergsneider | A61M 25/007 604/9 |

(Continued)

OTHER PUBLICATIONS

Merriam-Webster: oblong, https://web.archive.org/web/20170817101742/https://www.merriam-webster.com/dictionary/oblong, Accessed Mar. 7, 2023, Published Aug. 17, 2017. (Year: 2017).*

*Primary Examiner* — Ariana Zimbouski
(74) *Attorney, Agent, or Firm* — Hartman Global IP Law; Gary M. Hartman; Domenica N. S. Hartman

(57) ABSTRACT

Drainage devices have a self-clearing capability for reducing obstructions and a controllable flow restriction capability for controlling drainage flow, and microactuators for providing such capabilities. Such a microactuator includes a frame and an appendage anchored to the frame such that the frame supports the appendage, the frame at least partially surrounds the appendage, and the appendage is disposed in an opening or window defined by the frame. The appendage includes a platform and at least one beam that anchors the platform to the frame to enable the appendage to deflect out of a plane defined by the frame. The platform may include a ferromagnetic material that enables the appendage to deflect in response to an applied magnetic field.

21 Claims, 15 Drawing Sheets

(56) References Cited

U.S. PATENT DOCUMENTS

| | | | |
|---|---|---|---|
| 2011/0313340 A1* | 12/2011 | Judy | A61M 27/006 604/8 |
| 2013/0158464 A1* | 6/2013 | Samoocha | B08B 9/027 604/8 |
| 2017/0128702 A1* | 5/2017 | Yagi | A61M 25/1006 |

* cited by examiner

DRAINAGE DEVICES HAVING SELF-CLEARING AND FLOW RESISTANCE CONTROL CAPABILITIES, AND MICROACTUATORS FOR USE THEREWITH

CROSS-REFERENCE TO RELATED APPLICATIONS

This application claims the benefit of U.S. Provisional Application No. 62/653,904, filed Apr. 6, 2018, the contents of which are incorporated herein by reference.

BACKGROUND OF THE INVENTION

The present invention generally relates to drainage devices. The invention particularly relates to drainage devices for use in medical applications, including but not limited to drainage devices adapted for managing intraocular pressure (IOP) of patients, and to microactuators for use therewith and procedures for implanting and using such devices.

Glaucoma is a group of eye diseases that cause progressive damage to the optic nerve. It is commonly known as "the silent thief of sight" due to the lack of symptoms during the early stages. Due to the difficulty in early diagnosis, glaucoma is one of the leading causes of blindness and visual impairments in the world. Glaucoma affects around 64.3 million people in the world currently, which is expected to almost double by 2040. In the United States, there are more than 3 million patients with glaucoma, disproportionally affecting African Americans and Hispanics. The annual cost for glaucoma treatment in the US exceeds $2.9 billion.

Glaucoma is typically characterized by an increase in intraocular pressure (IOP) due to the imbalance between the production and outflow rates of aqueous humor (AH) from the anterior chamber to the anterior ciliary veins of the eye. In glaucoma patients, the AH outflow pathways (i.e., the trabecular meshwork, Schlemm's Canal, collector channels, aqueous veins, and episcleral veins) are often occluded, which can increase the IOP and subsequently damage the optic nerve over time.

Although there is no cure for glaucoma, the progression of disease can be significantly delayed using pharmaceutical and surgical interventions. The main goal of glaucoma therapies is to maintain a normal IOP range (generally about 10 to about 21 mmHg) to minimize optic nerve damage. Medications offer a very effective treatment for early stage glaucoma. Typically, glaucoma drugs are designed to decrease the production of AH or increase AH outflow through the trabecular meshwork or uveoscleral pathway. However, medications are often accompanied with several undesirable side effects including bitter taste, headache, conjunctivitis, visual blurring, eyelid inflammation, and eye pain. Surgical treatments such as trabeculectomy and laser trabeculoplasty can also be used to increase AH outflow. However, these surgical procedures may lead to serious post-operative complications such as hypotony (low IOP), cataracts, and bleb-related infections. The surgical ablation of the trabecular meshwork may result in coagulative necrotic tissue, which can cause complicate the chronic management of optimal AH outflow.

For patients with refractory or inflammatory glaucoma who are unresponsive to conventional pharmacological or surgical procedures, the implantation of glaucoma drainage devices (GDD) is often preferred due to better IOP control, ease of surgery, and minimum post-surgical complications in comparison to trabeculectomy. GDDs reduce IOP by facilitating the outflow of AH from the anterior chamber of the eye. Since the development of GDDs, various designs have been proposed with different functionalities. Although existing GDDs may differ in size, shape, and material, they typically comprise a thin reservoir ("foot"), typically a silicone plate, connected to a drain passage, typically a short polymeric tube that penetrates the anterior chamber of the eye to divert excess aqueous humor to the reservoir, which is typically placed at the equatorial region outside of the eyeball. GDDs can generally be categorized as either open tube or flow restrictive (valved) devices, the latter of which have an advantage over open tube designs by reducing the risk of early postoperative hypotony. A nonlimiting example of a GDD is represented in FIG. 1.

While GDDs have been successfully used to manage IOP for glaucoma patients for the past forty years, studies have reported that 15.1% of implanted GDDs fail within three years and more than 29.8% fail within five years post-implantation. Clinical studies have shown that up to 10% of glaucoma patients required additional surgical intervention because of tube blockage, typically as a result of biofouling of the tube lumen. Hydrophobic polymer materials from which GDDs are usually constructed (as examples, polypropylene, polymethylmethacrylate (PMMA), and polydimethylsiloxane) typically have a high affinity for interstitial proteins such as fibrinogen, IgG, and albumin that adsorb onto the interior surface of the tube within minutes after implantation. Once formed, the proteinaceous biofilm often triggers an inflammatory response that can lead to premature device failure. Existing GDD designs have not fully addressed the issue of biofouling.

An additional issue concerning GDDs relates to a lack of flow resistance control, which can lead to hypotony due to overdrainage of AH. Though flow restrictive GDDs utilize a built-in valve to prevent overdrainage, the flow restriction is fixed for a specific pressure threshold and cannot be adjusted to adequately address daily and long-term IOP fluctuations that occur in glaucoma patients.

BRIEF DESCRIPTION OF THE INVENTION

The present invention provides drainage devices have a self-clearing capability for reducing obstructions and a controllable flow restriction capability for controlling drainage flow, and microactuators for providing such capabilities. The devices are particularly well suited for use medical drainage passages, including but not limited to drainage passages of glaucoma drainage devices (GDDs) adapted for managing intraocular pressure (IOP) of patients. In such applications, the microactuators are preferably operable to combat biofouling, control flow resistance, and enable the personalization of the device for various levels of intraocular pressure.

According to one aspect of the invention, a microactuator adapted for inhibiting the formation of obstructions in a drainage passage includes a frame and an appendage anchored to the frame such that the frame supports the appendage, the frame at least partially surrounds the appendage, and the appendage is disposed in an opening or window defined by the frame. The appendage includes a platform and at least one beam that anchors the platform to the frame to enable the appendage to deflect out of a plane defined by the frame. The platform includes a ferromagnetic material that enables the appendage to deflect in response to an applied magnetic field.

According to other aspect of the invention, methods and drainage devices are provided that entail operating a microactuator to inhibit the formation of obstructions in a drainage passage.

Technical aspects of drainage devices as described above preferably include the ability to address reliability issues of glaucoma drainage devices relating to biofouling during implantation, improved functionality due to the ability to provide variable flow resistance, and the ability to customize functionality for a wide range of patients.

Other aspects and advantages of this invention will be appreciated from the following detailed description.

BRIEF DESCRIPTION OF THE DRAWINGS

The application contains at least one drawing executed in color.

FIG. 8 contains graphs, the lefthand graph plotting theoretical and measured angular deflections of an appendage of a microactuator when subjected to an increasing applied magnetic field (n=3), and the righthand graph plotting frequency responses of an appendage of a microactuator when vibrated in water (scale bar=500 micrometers) as a result of being subjected to a time-varying magnetic field. FIG. 9 contain images depicting shear stress distributions generated on surfaces of, respectively, a microactuator and a tube in which the microactuator is placed (t=173 ms). FIG. 10 plots maximum shear stresses in the microactuator and tube as a function of actuation time.

FIG. 11 is a graph plotting the relationship between the concentration of a protein solution (two hours of incubation) and the adsorption of a BSA-FITC biofilm on the lumen surface (n=5 for each concentration). FIG. 11 further contains fluorescence images of a microactuator appendage subjected to a time-varying magnetic field to vibrate at 20 Hz and at different out-of-plane amplitudes over a period of thirty seconds or five minutes. FIG. 12 contains a bar graph evidencing film clearing capabilities of the vibrating microactuator appendages of FIG. 11 indicated by a decreasing fluorescence intensity (n=3 for each). FIG. 12 further contains images evidencing the removal of a BSA-FITC film from a lumen of a microtube using a vibrating microactuator located within the lumen. FIGS. 13 and 14 contain images and a bar graph showing fluorescence intensities (dotted box) of BSA-FITC films on surfaces of microtube lumens and evidencing a decreasing fluorescence intensity near a microactuator located within one of the lumens.

DETAILED DESCRIPTION OF THE INVENTION

The following describes drainage devices that incorporate microactuators to enable a self-clearing capability for reducing obstructions in a drain passage and a controllable flow restriction capability for controlling drainage flow in the passage. Particular but nonlimiting embodiments of the drainage devices are configured as glaucoma drainage devices (GDDs) and are capable of mechanically inhibiting the formation of obstructions and removing obstructions, for example, as a result of biofouling, within a drainage tube of the device by operating the microactuators to generate shear stresses in the aqueous humor (AH) fluid flowing from the anterior chamber of the eye through the tube. Additionally, particular but nonlimiting embodiments of the drainage devices are capable of providing and controlling restriction to flow through a drainage tube of a glaucoma drainage device by controlling which microactuators are operated and the extent to which the operated microactuators are actuated into the passageway of the tube. Though the following discussion will describe microactuators as placed within drainage tubes of medical devices, it should be understood that the invention is not restricted to medical devices or placement within tubes, and instead the microactuators could be placed in flow passages formed by other means for use in a wide variety of fluid-handling devices.

The microactuators can be fabricated from various materials, as nonlimiting examples, biocompatible polymers including liquid crystal polymer (LCP) films, poly(vinylidene fluoride) (PVDF), polyimides, parylene, etc., and using various processes, for example, by maskless photolithography, microfabrication techniques of the types used to produce microelectromechanical systems (MEMS), etc. Mechanical actuation of the thin-film microactuators is induced by magnetic means, which as used herein can be any device capable of generating a magnetic field of sufficient strength to induce a mechanical response of the device that can be controlled by adjusting the strength of the applied magnetic field. As such, the microactuator can be actuated in a static manner to cause an appendage thereof to deflect partially or fully into a flowpath of a fluid flowing within the lumen of a drainage tube, such that the degree to which the microactuator creates a flow restriction within the lumen can be controlled. In addition, the microactuator can be actuated in a dynamic manner (for example, oscillated or vibrated) such that obstructions, including those caused by biofouling, may be prevented or removed without surgical intervention.

Figure 1:
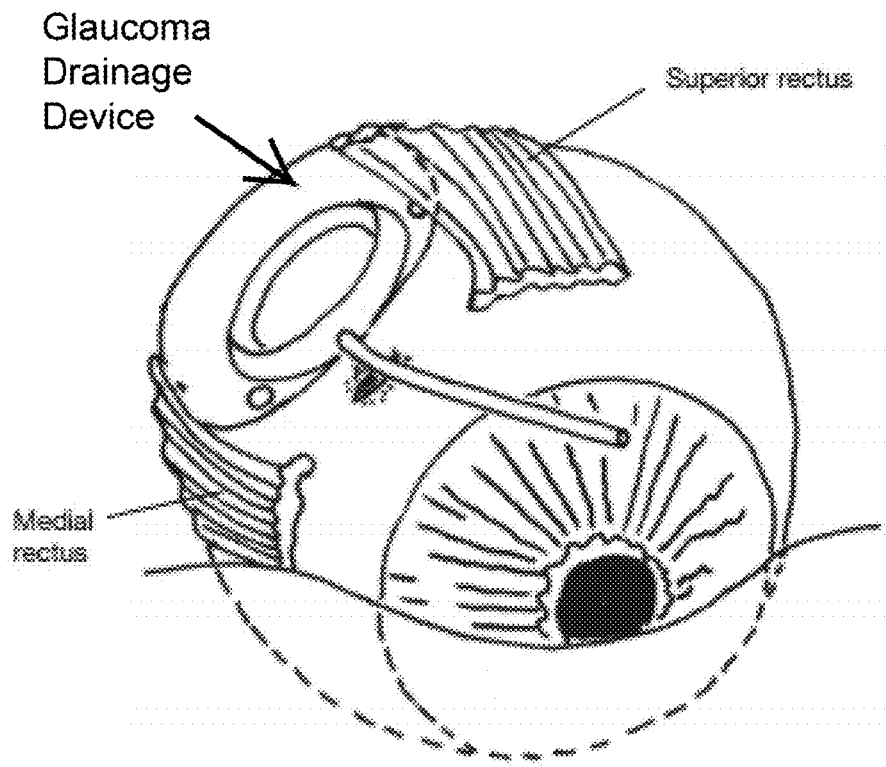
FIG. 1 schematically represents a nonlimiting example of a glaucoma drainage device of a type known in the art.
Figure 2:
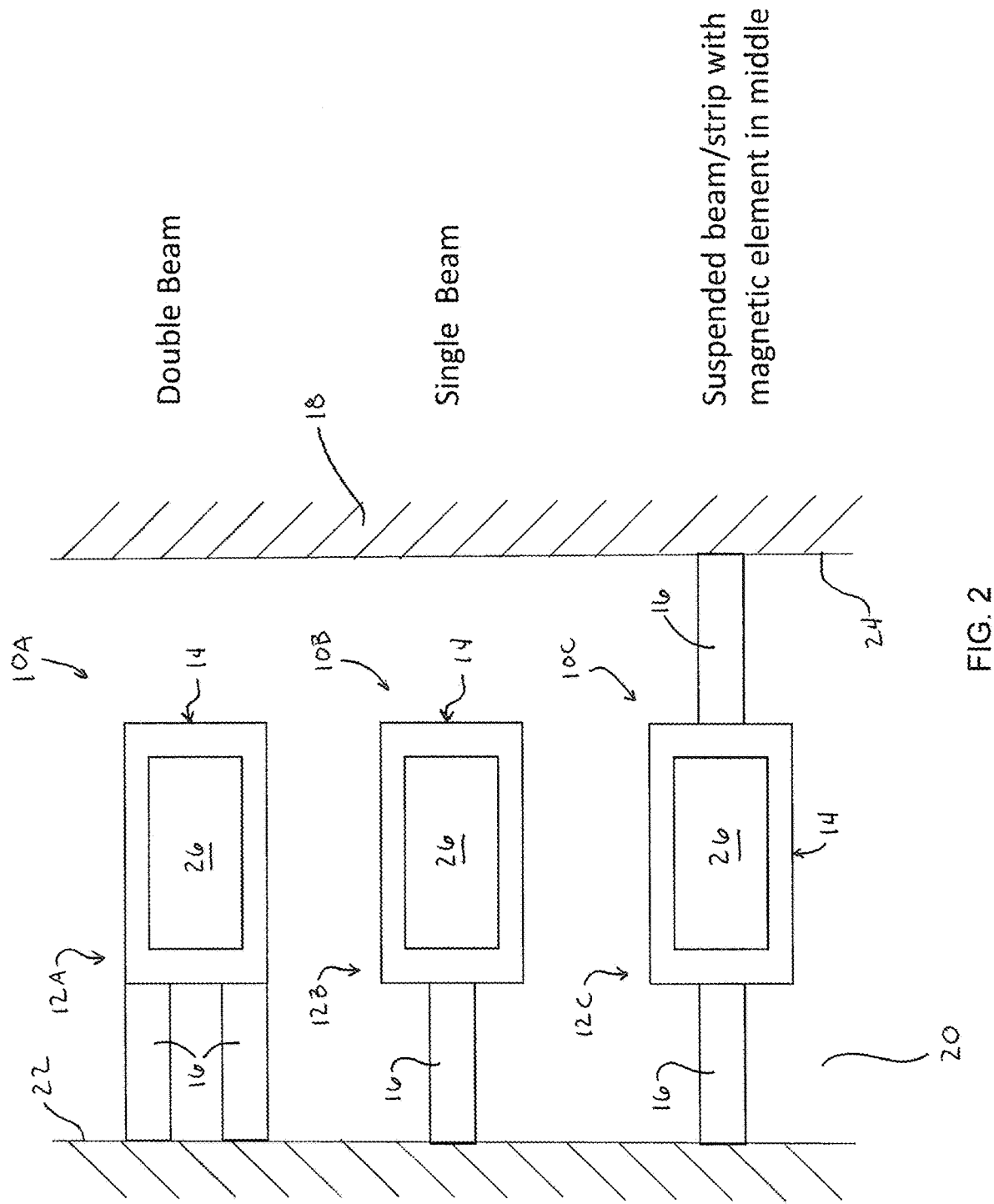
FIG. 2 schematically represents nonlimiting examples of microactuators adapted to provide self-clearing and flow control capabilities for a drainage device in accordance with nonlimiting embodiments of this invention.

FIG. 2 schematically represents three nonlimiting configurations of appendages 12A, 12B, and 12C of microactuators 10A, 10B, and 10C. Each appendage 12A, 12B, and 12C comprises a platform 14 and one or more beams 16 that connect the platform 14 to one or more walls of a frame 18, so that the appendages 12A, 12B, and 12C are suspended in a flow passage 20. The appendages 12A and 12B are cantilevered as a result of being attached to a single wall 22 of the frame 18. The appendage 12A is attached to the wall 22 with two parallel beams 16, whereas the appendage 12B is attached to the wall 22 with a single beam 16. The appendage 12C is suspended between the wall 22 and an oppositely-disposed second wall 24 of the frame 18 by two collinear beams 16. Two or more parallel beams 16 are believed to be preferred to promote the dynamic stability of the appendage 12A and inhibit the appendage 12A from twisting during actuation, though it is foreseeable that for some applications the single beam 16 or collinear beams 16 could be employed and some degree of twisting allowed or even desired. Each appendage 12A, 12B, and 12C further comprises a magnetic element 26 on its platform 14. As a result, mechanical actuation of the appendages 12A, 12B, and 12C can be induced by applying a magnetic field whose strength can be adjusted to control the mechanical responses of each microactuator 10A, 10B, and 10C. For example, each microactuator 10A, 10B, and 10C can be actuated to cause its appendage 12A, 12B, and 12C to deflect partially or fully into the passage 20 such that the degree to which the microactuators 10A, 10B, and 10C create a flow restriction within the passage 20 can be controlled. Though represented as rectangular, the shapes of the platforms 14 of the microactuators 10A, 10B, and 10C may be tailored to at least partially match the cross-sectional shape of the passage 20, for example, a rounded distal edge that is complementary to a passage 20 having a round interior cross-sectional shape.

Figure 3:
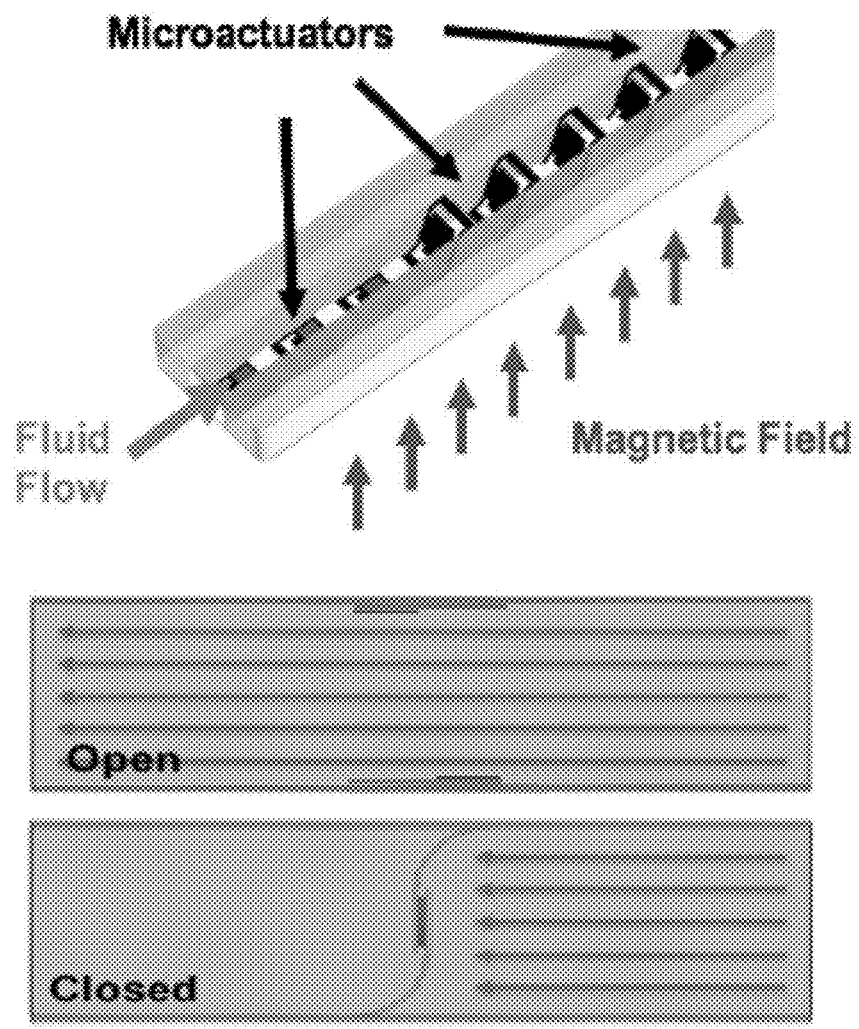
FIG. 3 schematically represents certain structural and operational characteristics of microactuators configured in accordance with a nonlimiting embodiment of this invention.

FIG. 3 schematically represents a nonlimiting example of a drainage device in which two rows of opposing microactuators are arranged within a frame comprising top, bottom, and side walls. The upper image in FIG. 3 is a perspective view with the top and bottom walls omitted to reveal a flow passage between the side walls. The middle and lower images of FIG. 3 show one pair of opposing microactuators attached to the top and bottom walls. As with the appendages 12A and 12B of FIG. 2, each appendage shown in FIG. 3 is a cantilever, comprises a platform connected to either the top or bottom wall of the frame with one or more beams, and has a magnetic element carried on its platform. The middle image shows an "Open" state in which the appendages of the opposing microactuators are not deflected into the flow passage, whereas the bottom image shows a "Closed" state in which the appendages have been statically deflected (actuated) into the passage as a result of the application of a magnetic field. In the lower image, the magnetic field strength is sufficient to cause the appendages to fully deflect until they contact each other within the passage. Alternatively, a lesser magnetic field could be applied so that the flow passage is only partially closed as a result of the appendages being partially deflected into the passage. The extent to which each appendage deflects into the passage can also be modified for a given magnetic field strength by tailoring the magnetic element disposed on the appendage, e.g., the types of materials, size and shape of the element, etc., and/or tailoring the stiffness of the appendage, e.g., the material, thickness, number of beams material, etc. For example, assuming a uniform magnetic field strength in the upper image of FIG. 3, those appendages shown as not being deflected may be a result of having smaller or weaker magnetic elements and/or stiffer beams. As such, the performance of a drainage device can be tailored by tailoring the responses of its microactuators, so that each microactuator or any group of microactuators can be individually addressed. In doing so, appendages in the statically closed and partially closed states are able to provide different levels of flow restriction for a fluid flowing through the flow passage, with flow restriction increasing with the degree of deflection of any one or more appendages as well as the number of appendages deflected. In addition, the appendages are able to generate different levels of shear stresses in the fluid to inhibit and/or remove biofouling from the walls of the frame. The latter offers a self-clearing capability that, as discussed below, can be promoted by inducing motion in the appendages, e.g., oscillation, vibration, etc.

In view of the above, a drainage device that incorporates microactuators in a manner similar or equivalent to what has been described above may be employed as a "smart" glaucoma drainage device with an array of individually addressable flow-resistant microactuators having the ability to control overdrainage by selectively statically deflecting any one or more of the microactuators to increase flow resistance, and/or selectively inducing dynamic movement in any one or more of the microactuators to inhibit or remove biofouling. Such a glaucoma drainage device can not only exhibit improved reliability by addressing biofouling-related shunt failures, but will provide a more personalized therapy for individual glaucoma patients by allowing non-invasive post-implanted adjustment of AH flowrate.

Figure 4:
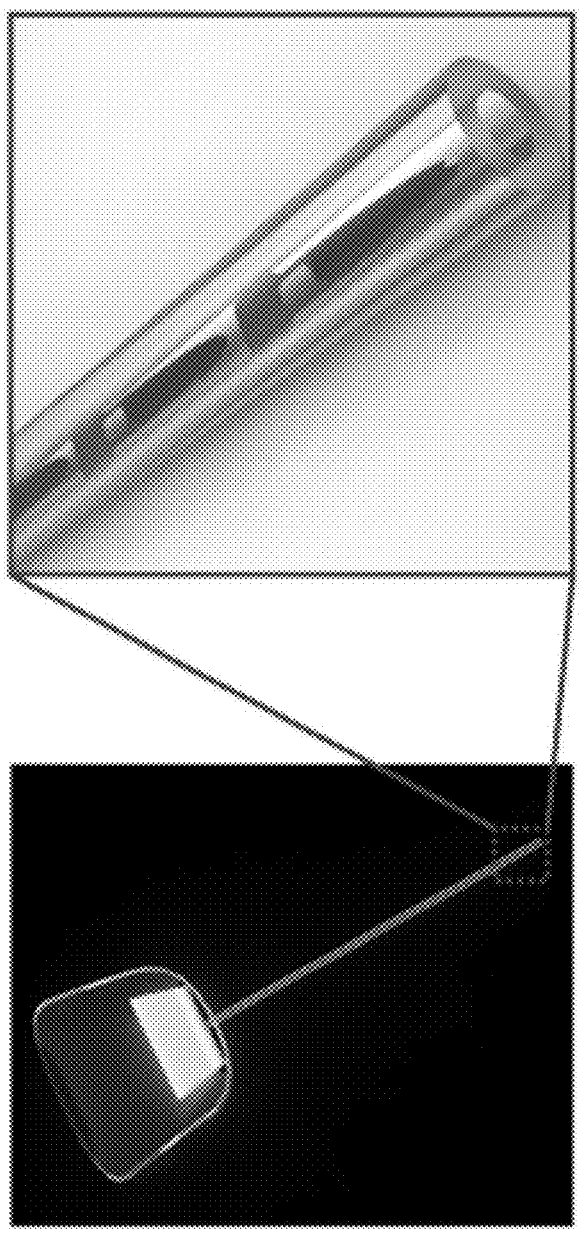
FIG. 4 contains two images of a glaucoma drainage device equipped with multiple microactuators adapted to provide self-clearing and flow restriction capabilities for the device in accordance with a nonlimiting embodiment of this invention.

The following will describe the design, fabrication, and testing of certain embodiments of drainage devices configured as glaucoma drainage devices to actively combat the buildup of a proteinaceous biofilm on the interiors of drainage tubes and control flow resistance through the tubes. Though various materials and fabrication methods may be used as noted above, the particular but nonlimiting examples described below were fabricated by patterning copper-cladded liquid crystal polymer (LCP) films using maskless photolithography to yield a rapid-prototyping process capable of reducing costs and increasing manufacturing throughput. FIG. 4 depicts such a device comprising a thin reservoir (plate or foot) connected to a tube (sometimes referred to herein as a microtube). The tube has a microscale lumen (internal diameter of about 300 micrometers). Both the reservoir and tube are formed of biocompatible materials, nonlimiting examples of which include polymeric materials such as silicone, polypropylene, polymethylmethacrylate, polydimethylsiloxane, etc. The reservoir is adapted to be placed outside of an eye and the tube is adapted to penetrate the anterior chamber of the eye to divert excess aqueous humor to the reservoir, where one or more channels within the reservoir distribute the aqueous humor outside of the eye. FIG. 4 shows the tube as equipped with multiple thin-film microactuators located in its lumen. Additionally or instead, the microactuators can be located in one or more channels within the reservoir. In either case, the microactuators are configured to provide a self-clearing and controllable flow restriction capability for the device, namely, by applying a magnetic field to cause an appendage of one or more of the microactuators to deflect into the flowpath of aqueous humor flowing through the lumen and reservoir. The extent to which the appendage(s) deflect into the flowpath can be utilized to controllably restrict the flow of fluid through the lumen, and the deflection of the appendage(s) into the flowpath can also be controlled to generate shear stresses in the fluid to the extent that obstructions to flow in the lumen can be eliminated and/or inhibited from forming. For example, the microactuators shown in FIG. 4 have demonstrated a protein-clearing capability by externally applying time-varying magnetic fields, to the extent that surgical intervention to remove a proteinaceous biofilm would be unnecessary.

Figure 5:
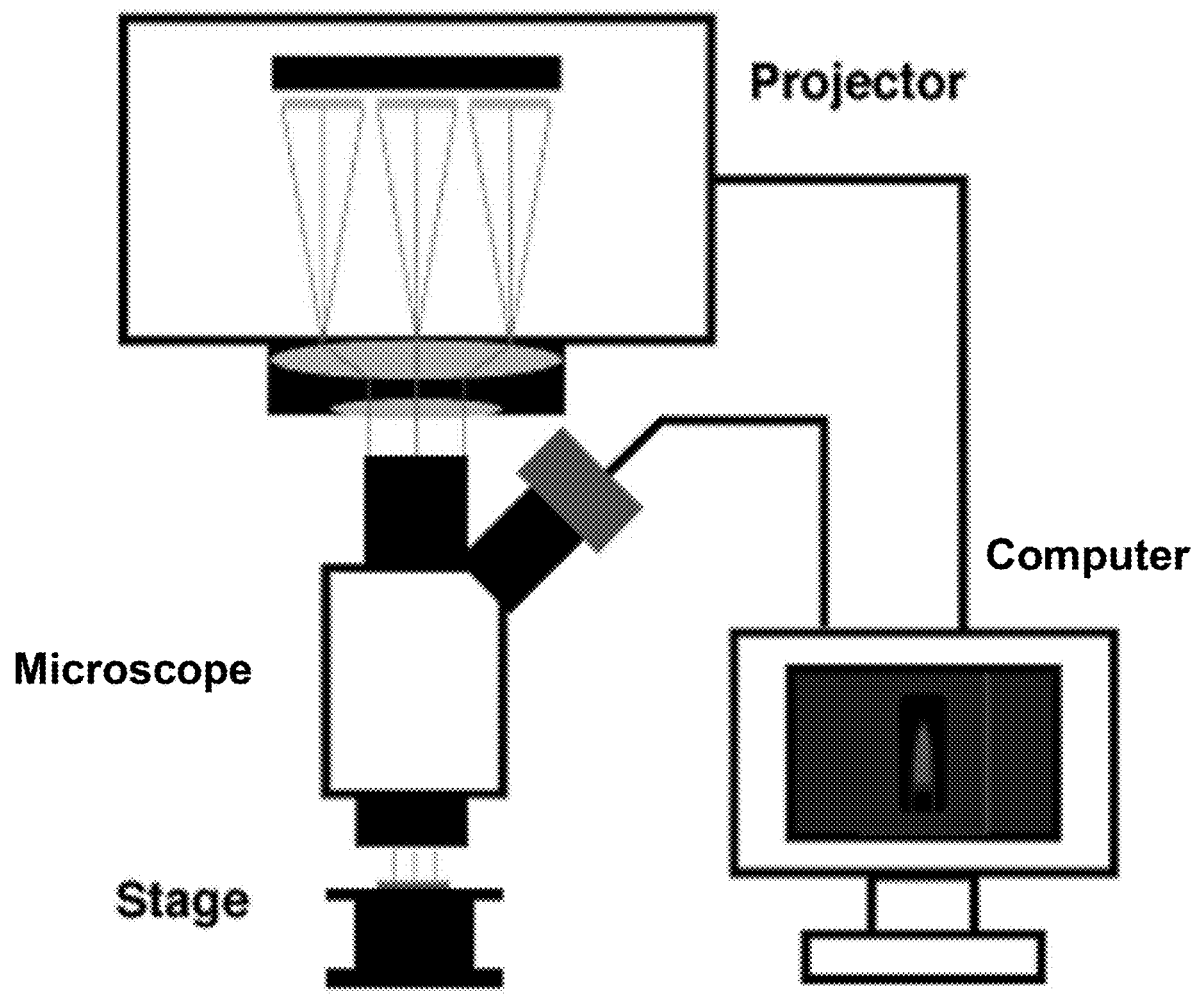
FIG. 5 schematically represents a maskless photolithography setup that was used for fabricating the microactuators of FIG. 4.

The magnetic microactuators depicted in FIG. 4 were fabricated using maskless photolithography on a double copper-cladded LCP sheet using a process represented in FIG. 5. Though the use of other biocompatible materials (including other polymeric materials) is foreseeable, LCPs have been used in biomedical applications with such beneficial features as low water absorption, biocompatibility, chemical resistance, and applicability to conventional microfabrication processes. In the example shown in FIG. 5, a computer is connected to a conventional projector with a digital micromirror device (HD142X, Optoma, Fremont, CA, USA) that was used to project and expose a desired pattern on a copper-cladded LCP sheet. The projector was vertically fixed on a stereo-microscope (SM-4B, Amscope, Irvine, CA, USA) using a bracket machined for this purpose. To improve resolution and reduce the size of the image, the alignment between the lens and the microscope between the sample stage and the projector were optimized. The mask pattern was designed and projected using Microsoft® PowerPoint® software. The exposure intensity was adjusted by modifying pattern color in the software.

Figure 6:
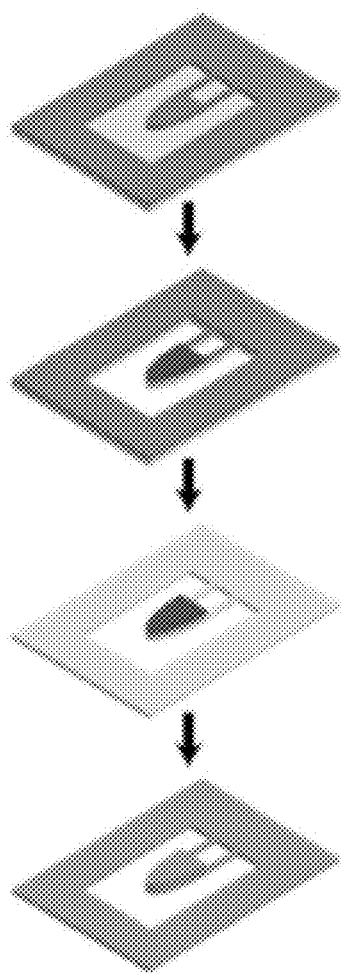
FIG. 6 schematically represents steps in the fabrication of the microactuators of FIG. 4 using the maskless photolithography setup of FIG. 5.

FIG. 6 illustrates the overall process flow (top image to bottom image) used to fabricate the microactuators seen in FIG. 4. As evident from FIG. 6, an individual microactuator is fabricated to comprise a cantilevered appendage anchored to a frame that surrounds and supports the appendage, such that the appendage is disposed in an opening or window defined by the frame. Though a single microactuator is shown, it should be understood that the process was used to simultaneously produce multiple microactuators in a single copper-cladded LCP sheet. A commercially available double copper-cladded LCP sheet (Ultralam 3850, Rogers Corporation, Chandler, AZ, USA) was obtained whose LCP layer had a thickness of about 25 micrometers. The copper cladding on one side of the sheet was completely removed using a wet copper etchant (CE-100, Transene, Danvers, MA, USA), after which the thickness of the LCP layer was reduced to about eight micrometers using a reactive ion etcher (PlasmaPro80, Oxford Instruments plc, Abingdon, Oxfordshire, United Kingdom). The appendage of the microactuator shown in the drawings is connected to the frame solely by the LCP sheet, and therefore thinning of the LCP layer had the effect of improving the compliance of the appendage. The resulting 8-μm-thick single-clad LCP sheet was then mounted onto a carrier wafer using a positive photoresist (PR) (AZ9260, Microchem, Westborough, MA, USA), with the copper cladding positioned on top of the sheet. The same photoresist material was then spin coated on the surface of the copper cladding, and the copper cladding was patterned using a maskless photolithography method. After etching the copper cladding using a wet copper etchant (CE-100, Transene, Danvers, MA, USA), the photoresist was removed using acetone to yield a cantilevered appendage, represented in the top image of FIG. 6. As evident from this image, the appendage comprised a platform and two parallel beams connecting the platform to the same edge of the frame. In addition, the platform had a rounded distal edge that was complementary to the round interior cross-sectional shape of the tube (FIG. 4) in which the microactuator was to be placed. Microactuators having appendages similarly configured to what is shown in FIG. 4 were subsequently evaluated during investigations discussed below.

Figure 7:
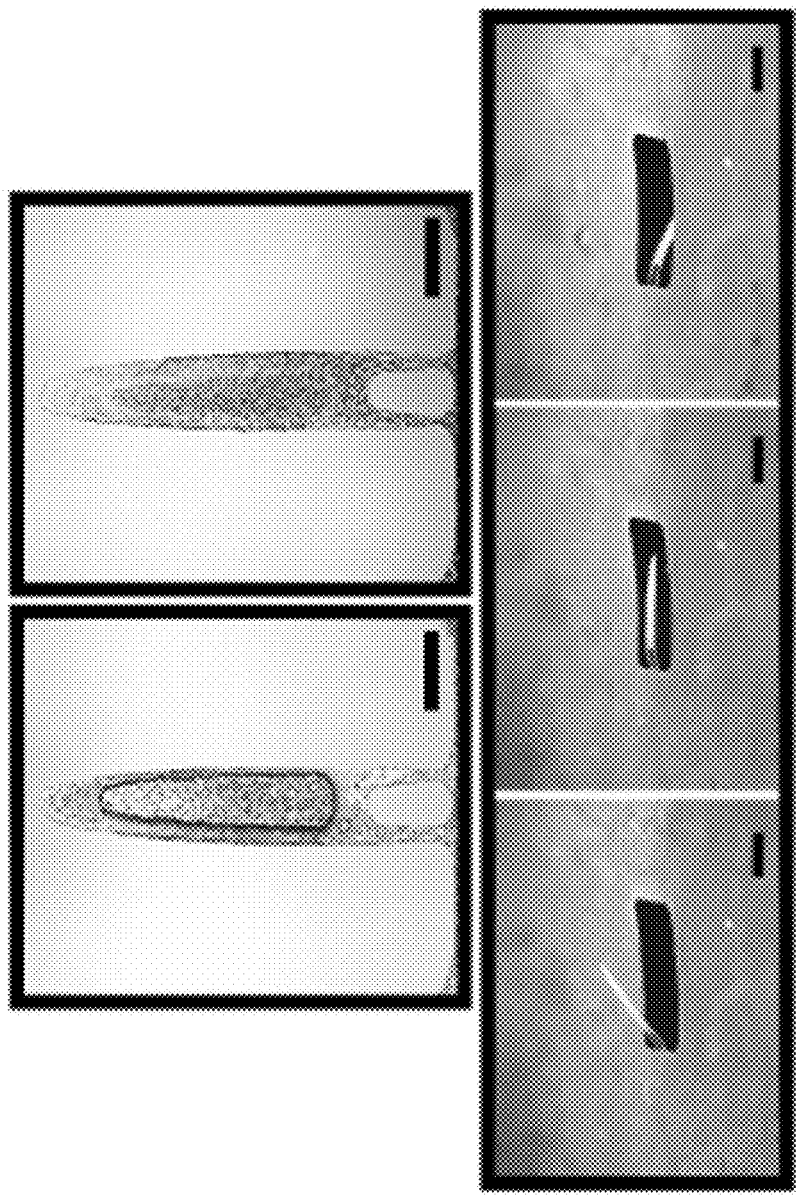
FIG. 7 contains two images showing microactuators (scale bar=200 micrometers) fabricated using the setup of FIG. 5 and process of FIG. 6, and three images showing the deflection of an appendage of a microactuator when subjected to different directional magnetic fields (11 kA/m) (scale bar=500 micrometers).

Magnet elements were then defined on the platform of the appendage using maskless photolithography. Various soft ferromagnetic materials may be used, and in the following examples nickel was used. Nickel was electroplated onto the platform to achieve a nickel film thickness of about 20 micrometers. After removing the photoresist (second image of FIG. 6), the appendage was released by etching the exposed portions of the LCP layer using a reactive ion etcher. The third image of FIG. 6 shows the result of removing the exposed copper layer on the beams and frame by a chemical etchant (BTP, Transene, Danvers, MA, USA). The bottom image of FIG. 6 shows the result of coating both sides of the microactuator with titanium using a sputterer (Magnetron sputtering systems, PVD Products, Inc., Wilmington, MA, USA) to improve biocompatibility. FIG. 7 contains images showing microactuators produced by the process described above. The upper two images depict an appendage, including its platform and two parallel beams connecting the platform to the frame (not shown). The lower three images show an appendage in three states induced by a magnetic field: deflected upward out of the plane of its frame (left image), in an undeflected (null) position approximately in the plane of its frame (center image), and deflected downward out of the plane of its frame (left image). As evident from these images, the entire appendage deflects relative to its frame by pivoting at a single linear pivot axis defined where its beams adjoin the frame.

To characterize the actuation capabilities of magnetic microactuators fabricated in the manner described above, the static and dynamic mechanical responses of the microactuators were evaluated. A magnetic moment of the soft ferromagnetic element is generated when the magnetic microactuator is placed in a static magnetic field. The microactuators can deflect out of plane (e.g., FIG. 7) when the direction of the applied magnetic field is normal to the surface of the magnetization direction of the magnet element. The deflection angle of the appendage of a microactuator can be described by $$\phi = \frac{v \cdot (\vec{M} \times \vec{H})}{k_\phi}$$

with the angular deflection $\Phi$, magnet volume v, magnetization $\vec{M}$, applied magnetic field $\vec{H}$, and the flexure stiffness $k_\Phi$. The beam geometry and the material property affect the mechanical stiffness of the flexure with following equation:

$$k_\phi = \frac{(E_c w t^3)}{12 l}$$

with the elastic modulus $E_c$, beam width w, beam thickness t, and beam length l.

Figure 8:
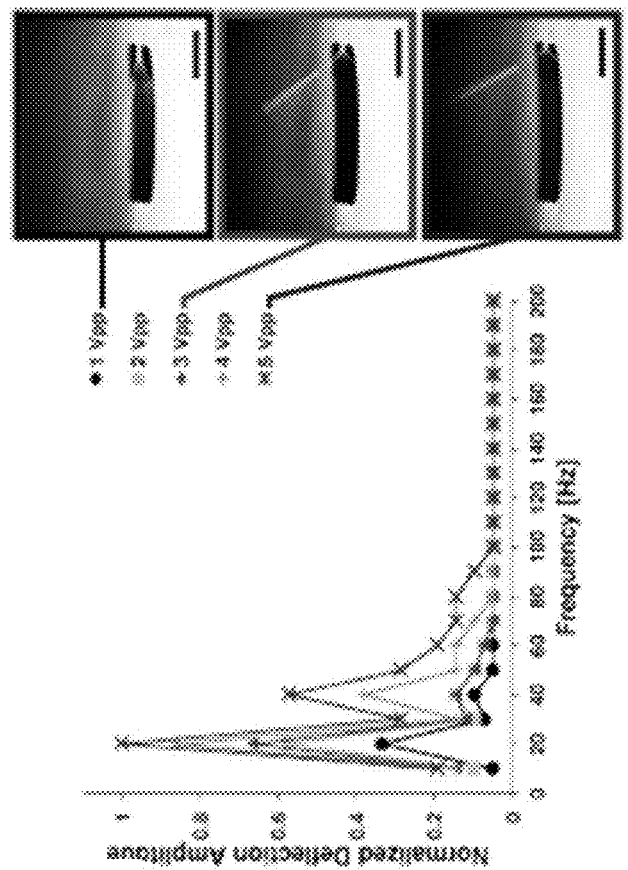
FIGS. 8 through 10 depict mechanical characterizations of a microactuator and finite element modeling of shear stress distribution.
Figure 8:
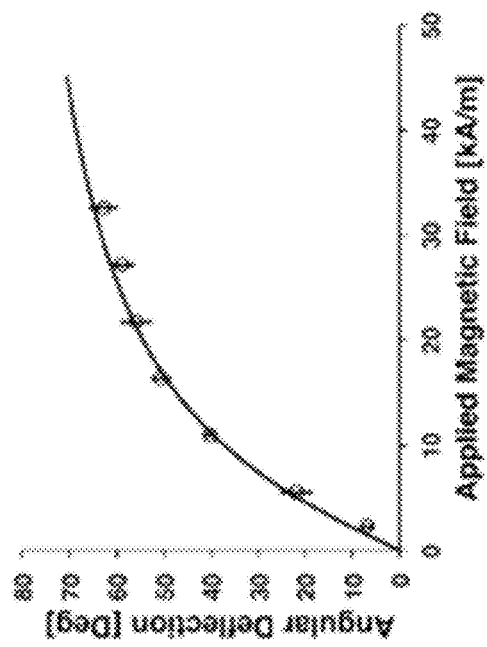

The static deflection angles of the appendages of the microactuators were measured in response to increasing static magnetic fields. The magnitudes of angular deflections were measured for a range of applied magnetic fields (0 to 35 kA/m). The external magnetic field was generated using a bespoke iron-core electromagnet. The strength of the magnetic field was quantified using a gaussmeter (Model 8010, Pacific Scientific OECO, Milwaukie, OR, USA). A microactuator was then placed on top of the electromagnet and the magnetic field was applied. Images of the deflected microactuators were taken using a digital microscope (KH8700, Hirox, Hackensack, NJ) and the deflection angles were measured from the images using ImageJ software. As shown in the lefthand graph of FIG. 8, the measured deflection angle of a microactuator was well matched with the theoretical deflection value in the same magnetic field range. The dynamic responses of the magnetic microactuators in water were measured using a customized laser deflecting setup. A laser beam was deflected by a mirror onto the nickel surface of a microactuator, which then reflected the laser beam onto a position sensitive diode sensor. The sensor sampled two-dimensional positions to a data acquisition system (LabView 2014, Austin, TX, USA). The time-varying magnetic field from a function generator was swept from 10 to 200 Hz at different applied voltages to obtain the frequency responses of the microactuators when vibrated (righthand graph in FIG. 8). From the results, it was determined that the highest deflection amplitude was obtained with an actuation (vibration) frequency of 20 Hz.

Figure 9:
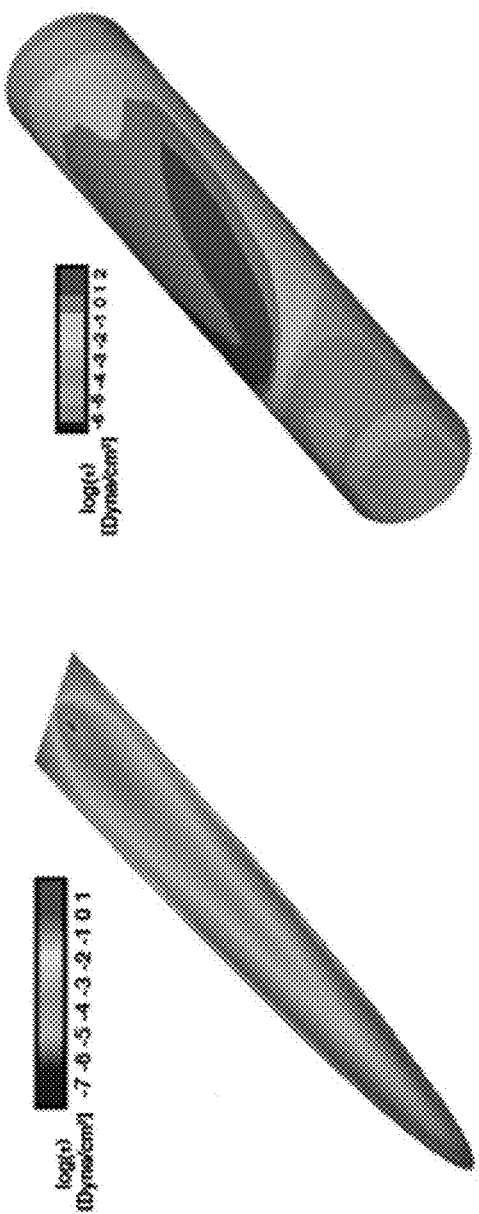
Figure 10:
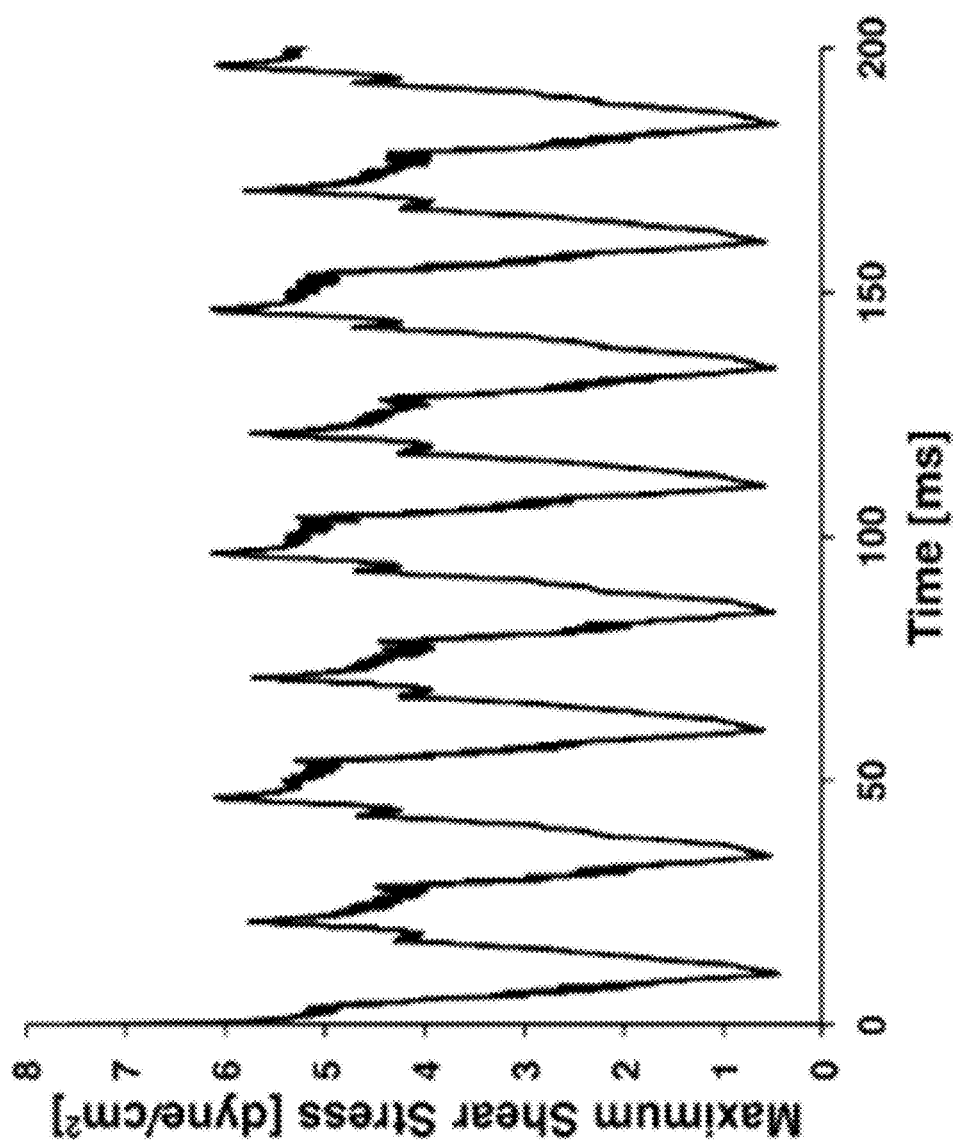

To determine shear stresses generated by actuating the microactuators, a finite volume method was used to simulate the shear stress on the surface of a microactuator and the lumen of the microtube by numerically solving Navier-Stokes equations (FIG. 9). The computational domain was discretized using a uniform, staggered, cartesian grid. An Euler explicit method was used for time discretization and spatial derivatives in convective and diffusive terms were computed using the quadratic upstream interpolation for convective kinematics and central difference schemes, respectively. Furthermore, the coupling between the pressure and velocity was conducted using a projection method. A distributed Lagrange multiplier method was implemented to simulate the motion of a microactuator in a viscous fluid, which allowed for accurately capturing the hydrodynamic interaction between the appendage of a microactuator and the surrounding fluid, and evaluating the shear stress acting on the surface. The simulation results showed that the maximum shear stress is generated at the edge of the microactuator appendage (lefthand image in FIG. 9). Actuation-induced shear stresses occurred in a microtube near the microactuator appendage when simulating the placement of the microactuator in a lumen of the microtube (righthand image in FIG. 9). During actuation, a maximum shear stress of approximately 6 dyne/cm$^2$ was periodically produced on the microactuator surface and tube surface (FIG. 10). These simulation results indicated that the surface area of a glaucoma drainage tube surrounding a microactuator can be cleaned by actuating (vibrating) the appendage of the microactuator.

The anti-biofouling performance of magnetic microactuators fabricated and simulated as described above was evaluated using fluorescent-tagged bovine serum proteins, specifically, fluorescein isothiocyanate (FITC) labeled bovine serum albumin (BSA) (BSA-FITC) (ThermoFisher Scientific, Waltham, MA, USA), which is known to readily adsorb onto and coat surfaces of polymeric glaucoma drainage tubes via non-specific binding and subsequently initiate an inflammatory response in vivo. To maximize the fluorescent intensity, various concentrations of BSA-FITC were incubated on Ti-coated LCP surfaces for two hours. Images of protein-coated samples were taken using a fluorescence microscope (Axio Observer Z1, Carl Zeiss Microscopy, LLC) using filter set 17 (excitation, BP 485/20, and emission BP 515-565, Carl Zeiss Microscopy, LLC) and quantified using ImageJ software (version 1.50i). The fluorescence intensity of adsorbed BSA-FITC plateaued at about 5 mg/ml (FIG. 11), and therefore all subsequent BSA-FITC evaluations were performed with this concentration.

Figure 15:
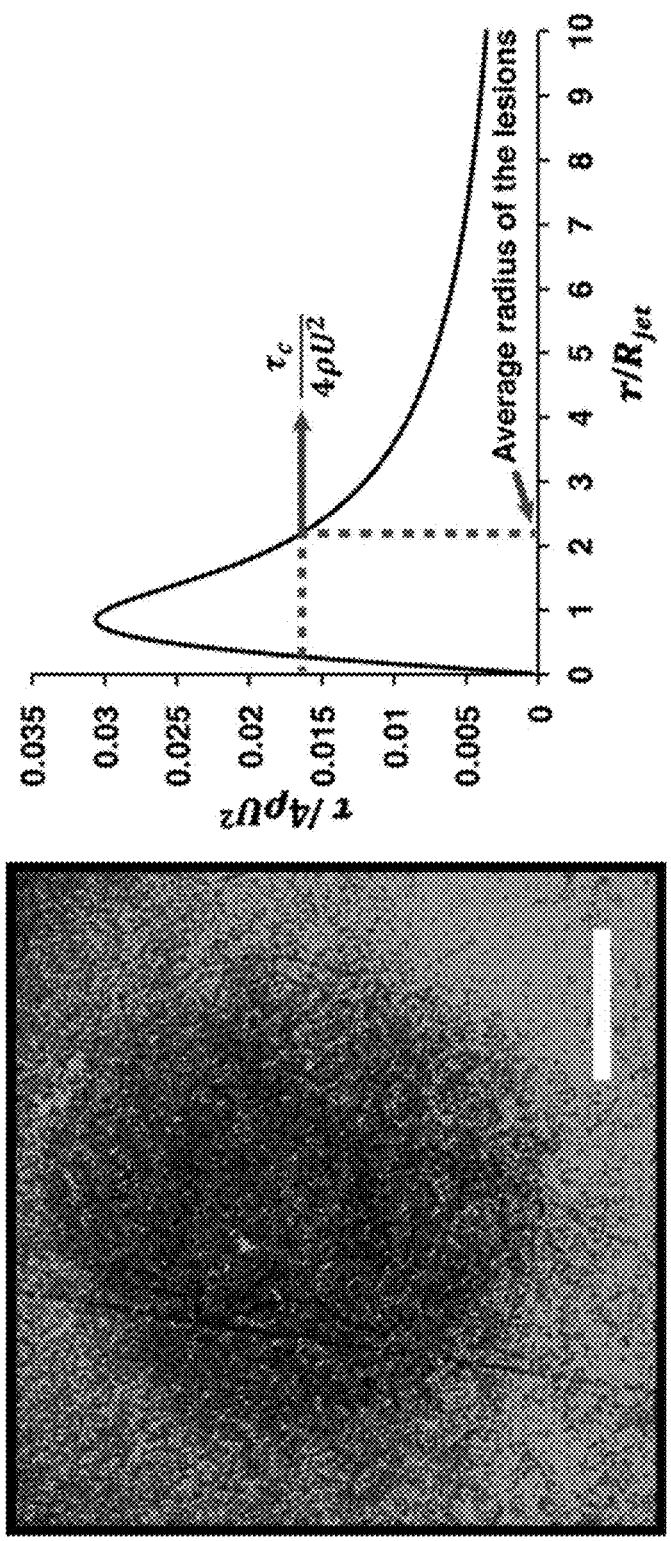
FIG. 15 contains an image showing a surface of a substrate from which a BSA-FITC film has been cleaned with a microactuator (scale bar=200 μm), and further contains a graph plotting nondimensional wall shear stress as a function of nondimensional radius from theoretical solution. The dotted line indicates the average value of the nondimensional wall shear stress obtained by the average value of the nondimensional radius of the lesions.

The magnitude of shear stress required to remove (desorb) absorbed protein on Ti-coated LCP surfaces was quantified via a jet impingement experiment. The jet impingement technique used was a type widely to analyze shear stresses for cell or bacteria attachment strength by correlating the size of a lesion created by a perpendicular jet of fluid which creates a well-characterized shear stress profile. The tip of a 15-ml syringe equipped with a needle having an inner diameter of 250 micrometers (7018333, Nordson EFD, East Providence, RI, USA) was vertically placed 1 mm over a BSA-FITC coated substrate and the jet flow was delivered using a syringe pump (NE-300, New Era Pump Systems, Inc., Farmingdale, NY, USA). To quantify the attachment shear stress of a BSA-FITC biofilm, the theoretical description of wall shear stress was used. The fluid jet was delivered at a flow rate of about 1.18 ml/min for five seconds, which corresponded to a Reynolds number of about 100. The fluid jet created a maximum shear stress of less than 30 dyne/cm$^2$ which is required to rupture a protein-ligand interaction. FIG. 15 contains an image showing a surface area of the substrate that has been cleaned of a BSA-FITC biofilm, and also contains a plot of non-dimensional wall shear stress as a function of non-dimensional radius for a fluid jet radius ($R_{jet}$) of 125 micrometers. The average radius for four lesions was about 284 micrometers, which was used to obtain the non-dimensional shear stress. The actual shear stress ($\tau_c$) to desorb a BSA-FITC biofilm, calculated from the non-dimensional shear stress value, was about 10.2 dyne/cm$^2$.

Figure 11:
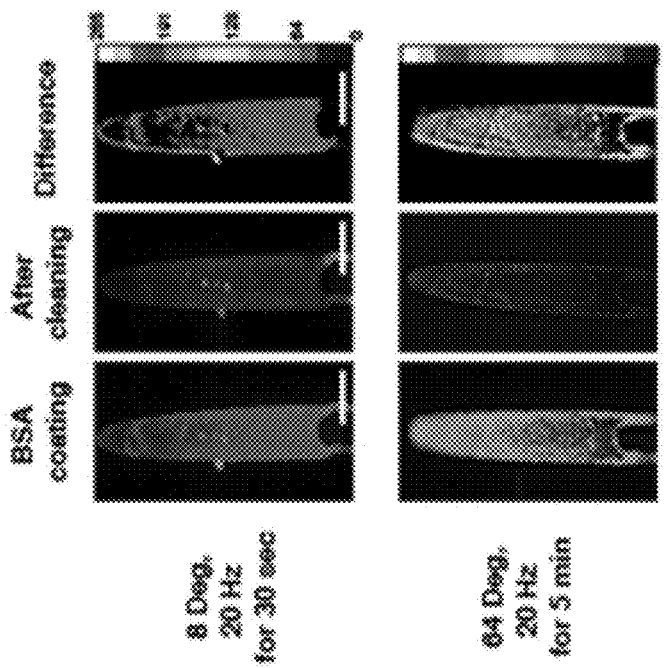
FIGS. 11 through 14 depict self-clearing characterizations of a lumen equipped with a microactuator and on whose surfaces a biofilm is present and cleared under different actuation conditions.
Figure 11:
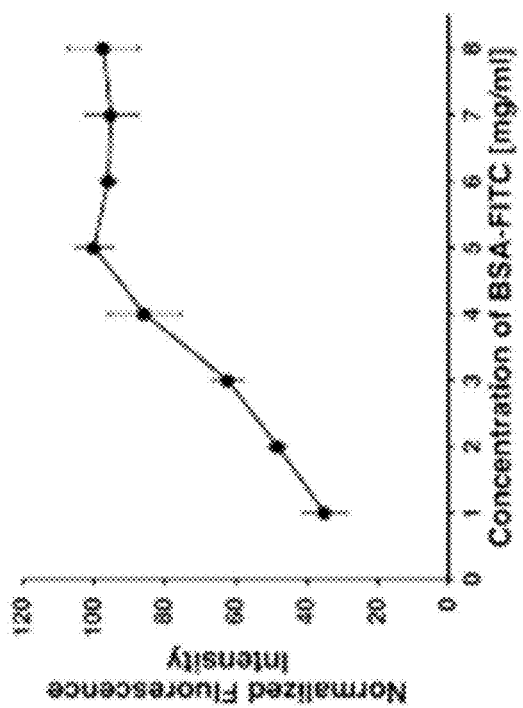
Figure 12:
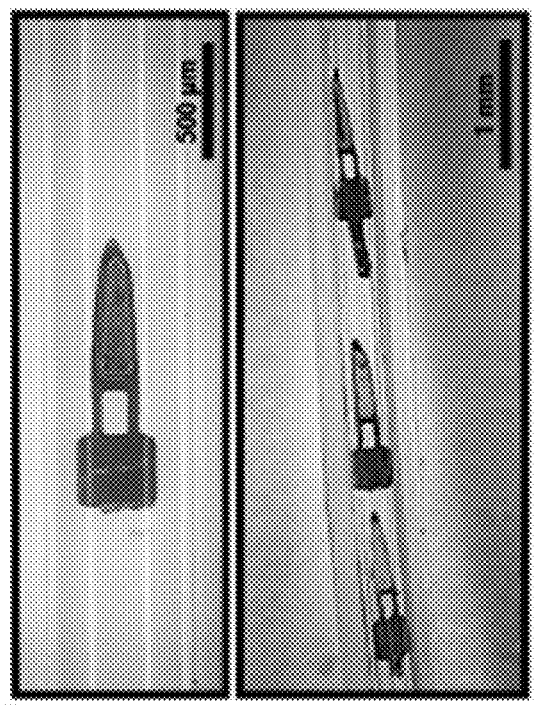
Figure 12:
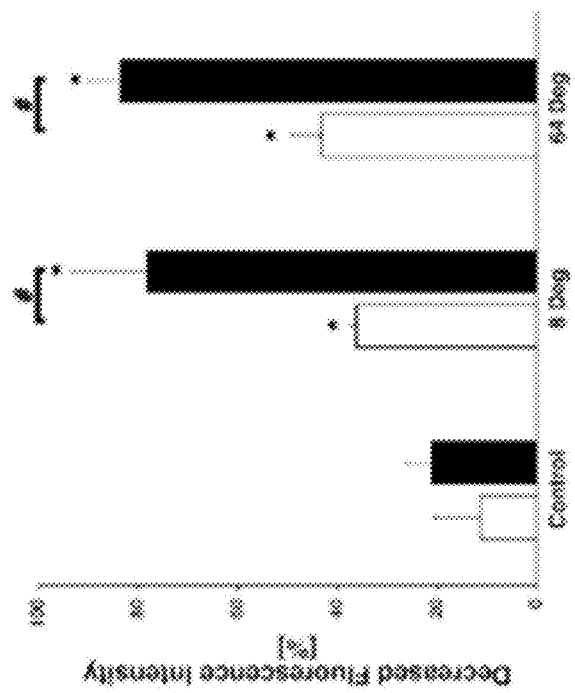
Figure 13:
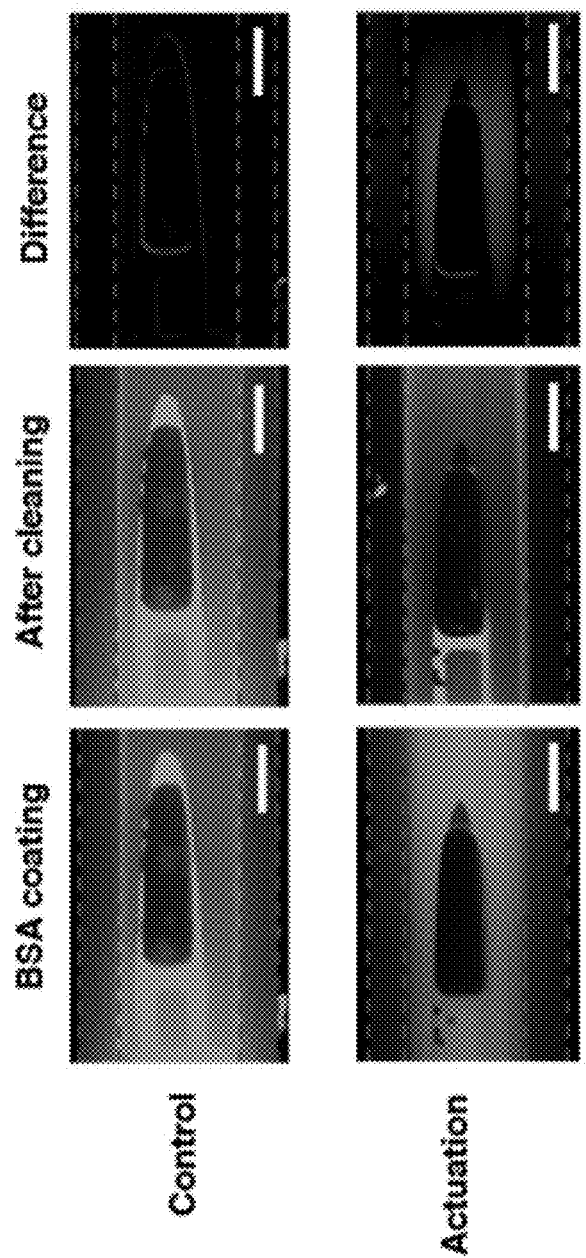
Figure 14:
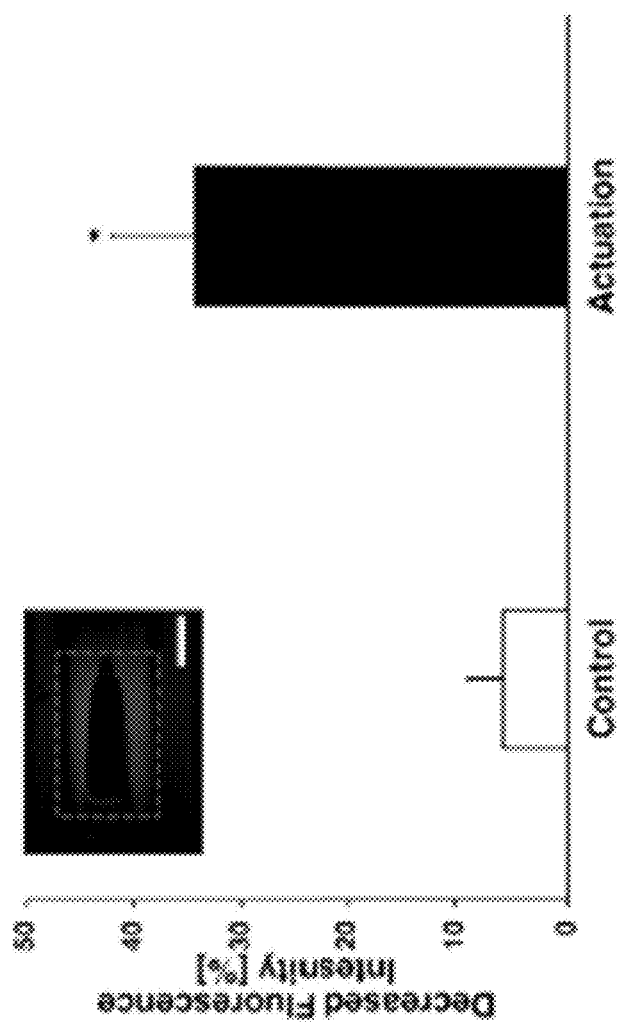

The impact of deflection amplitude and actuation duration on adsorbed protein concentration was then investigated with magnetic microactuators fabricated and simulated as described above. During actuation, each sample was placed in deionized water in a chamber that blocked ambient light. To compare the ability to clean a protein biofilm with the shear stress simulation results, fluorescence images of protein-coated microactuators were subtracted from images of the microactuators using the ImageJ software. The microactuators were actuated (vibrated) for about 30 seconds and about 5 minutes at about 20 Hz at two different angular deflection magnitudes (8 degrees and 64 degrees) using an externally applied magnetic field (n=3 for each). The decreased fluorescence intensity values were compared using one-way ANOVA with Tukey's HSD post-hoc analysis. As shown in FIGS. 11 and 12, the results indicated that BSA-FITC biofilms on the microactuators were significantly removed (desorbed) by actuation of (vibrating) their appendages regardless of deflection amplitude (p<0.01). However, the decreased intensity difference between small and large deflection magnitudes was not statistically significant. The effect of actuation duration on protein desorption was then evaluated by increasing the actuation time to 5 minutes (n=3 for each). FIG. 12 shows that there was significantly more protein desorption after 5 minutes of actuation compared to 30 seconds of actuation.

To demonstrate the ability of the microactuators to remove a protein biofilm from a polymeric tube of the type used in glaucoma drainage devices, microactuators fabricated and simulated as described above were anchored in PTFE (polytetrafluoroethylene) tubes as shown in FIG. 12. The insides of the tubes were coated with BSA-FITC and rinsed with deionized water at a flow rate of about 2.7 l/min, which is the typical flow rate of aqueous humor in human eyes. The microactuators were actuated for 5 minutes at 20 Hz to desorb the BSA-FITC biofilms from the tube surfaces. As shown in FIG. 12, the BSA-FITC biofilms near the microactuators were at least partially removed by actuation. The decreased fluorescence intensities from the ends of the beams to the tips of the appendages were quantified and compared using one-way ANOVA with Tukey's HSD post-hoc analysis. The results showed that the actuation had significantly removed the BSA-FITC biofilms on the tube interior walls.

On the basis of the above investigations, it was concluded that magnetic microactuators of types configured as described above and/or shown in the drawings should be capable of being integrated into the lumen of a glaucoma drainage device to prevent the lumen from becoming obstructed. Both static and dynamic responses suggested good control of the fabrication processes, and the in vitro evaluation using BSA-FITC showed that the actuation of the microactuators can remove proteinaceous biofouling on surfaces of the microactuators and the microtubes in glaucoma drainage devices. It is believed that the microactuators can be integrated within a microshunt of a glaucoma drainage device to combat bacterial or cell attachment and blood product.

While the invention has been described in terms of particular embodiments and investigations, it should be apparent that alternatives could be adopted by one skilled in the art. For example, the drainage devices, drainage tubes, and microactuators could differ in appearance and construction from the embodiments described herein and shown in the drawings, functions of certain components of the drainage devices, drainage tubes, and microactuators could be performed by components of different construction but capable of a similar (though not necessarily equivalent) function, and appropriate materials could be substituted for those noted. In addition, the above detailed description is intended to describe the particular embodiments represented in the drawings and certain but not all features and aspects thereof, and to identify certain but not all alternatives to the embodiments and described features and aspects. As a nonlimiting example, the invention encompasses additional or alternative embodiments in which one or more features or aspects of a particular embodiment could be eliminated or two or more features or aspects of different embodiments could be combined. Accordingly, it should be understood that the invention is not necessarily limited to any embodiment described herein or illustrated in the drawings, and the phraseology and terminology employed above are for the purpose of describing the illustrated embodiments and investigations and do not necessarily serve as limitations to the scope of the invention. Therefore, the scope of the invention is to be limited only by the following claims.

The invention claimed is:

1. A microactuator adapted for inhibiting the formation of obstructions in a drainage passage that has a round interior cross-sectional shape, the microactuator comprising:
   a frame; and
   an appendage anchored to and cantilevered from the frame such that the frame supports the appendage, the frame at least partially surrounds the appendage, and the appendage is disposed in an opening or window defined by the frame, the appendage comprising a platform and at least one beam that anchors the platform to the frame to enable the appendage to deflect relative to the frame, the platform comprising a ferromagnetic material that enables the appendage to deflect in response to an applied magnetic field;
   wherein the platform is connected at a first end thereof to the at least one beam, has a second end that is oppositely disposed from the first end, and has a rounded distal edge at the second end having a parabolic shape that is complementary to the round interior cross-sectional shape of the drainage passage.

2. The microactuator according to claim 1, wherein the at least one beam of the appendage is formed of a biocompatible material.

3. The microactuator according to claim 1, wherein the appendage is anchored to the frame solely by the at least one beam.

4. The microactuator according to claim 1, wherein the frame has an edge and the at least one beam of the microactuator adjoins the edge of the frame to define a single linear pivot axis for the appendage.

5. The microactuator according to claim 1, wherein the platform further comprises a polymeric film and the ferromagnetic material overlies the polymeric film.

6. The microactuator according to claim 1, further comprising magnetic means for generating a magnetic field that causes the appendage to deflect relative to the frame.

7. The microactuator according to claim 6, wherein the magnetic means is configured to apply the magnetic field at different strengths to control an extent to which the appendage deflects.

8. The microactuator according to claim 6, wherein the magnetic means is configured to apply the magnetic field as a time varying magnetic field to induce dynamic motion in the appendage.

9. The microactuator according to claim 1, wherein the microactuator is one of a plurality of microactuators and at least one microactuator of the plurality of microactuators or at least one group of microactuators of the plurality of microactuators has a different static and/or dynamic response to the magnetic field than at least one other microactuator of the plurality of microactuators or at least one other group of microactuators of the plurality of microactuators.

10. The microactuator according to claim 1, wherein the microactuator is disposed in the drainage passage and the drainage passage is a channel within a reservoir of a glaucoma drainage device or a lumen within a drainage tube of a glaucoma drainage device.

11. A drainage device comprising:
   a drainage passage that has a round interior cross-sectional shape;
   at least one microactuator disposed in the drainage passage; and
   magnetic means for statically or dynamically actuating the at least one microactuator to inhibit the formation of flow obstructions in the drainage passage;
   wherein the at least one microactuator comprises a frame and a cantilevered appendage anchored to the frame such that the frame supports the appendage, the frame at least partially surrounds the appendage, and the appendage is disposed in an opening or window defined by the frame, the appendage comprising a platform and a beam that anchors the platform to the frame to enable the appendage to deflect relative to the frame, the platform comprising a ferromagnetic material that enables the appendage to deflect in response to an applied magnetic field; and
   wherein the platform is connected at a first end thereof to the at least one beam, has a second end that is oppositely disposed from the first end, and has a rounded distal edge at the second end having a parabolic shape that is complementary to the round interior cross-sectional shape of the drainage passage.

12. The drainage device according to claim 11, wherein the at least one microactuator comprises at least two beams that anchor the platform to the frame.

13. The drainage device according to claim 11, wherein the at least one microactuator is one of a plurality of microactuators and the at least one microactuator or at least one group of microactuators of the plurality of microactuators has a different static and/or dynamic response to the magnetic field than at least one other microactuator of the plurality of microactuators or at least one other group of microactuators of the plurality of microactuators.

14. The drainage device according to claim 11, wherein the drainage device is a glaucoma drainage device and the drainage passage is a channel within a reservoir of the glaucoma drainage device or a lumen within a drainage tube of the glaucoma drainage device.

15. A method of inhibiting the formation of obstructions in a drainage passage and restricting flow of a fluid flowing through the drainage passage, the method comprising:
placing at least one microactuator of claim 1 within the drainage passage; and
actuating the appendage of the at least one microactuator by applying a magnetic field.

16. The method according to claim 15, wherein the drainage passage is a medical drainage passage and the fluid is a biological fluid.

17. The method according to claim 15, wherein applying the magnetic field causes the appendage of the at least one microactuator to vibrate and periodically deflect into and out of a flowpath of the fluid flowing through the drainage passage.

18. The method according to claim 15, wherein the at least one microactuator is one of a plurality of microactuators and the at least one microactuator or at least one group of microactuators of the plurality of microactuators has a different static and/or dynamic response to the magnetic field than at least one other microactuator of the plurality of microactuators or at least one other group of microactuators of the plurality of microactuators.

19. The method according to claim 15, wherein the at least one microactuator is disposed in the drainage passage and the drainage passage is a channel within a reservoir of a glaucoma drainage device or a lumen within a drainage tube of a glaucoma drainage device.

20. The method according to claim 15, wherein the magnetic field is applied as a time varying magnetic field to dynamically deflect the appendage of the microactuator and cause the appendage to periodically deflect into and out of a flowpath of the fluid within the drainage passage.

21. The method according to claim 15, wherein applying the magnetic field causes the appendage of the at least one microactuator to selectively partially or fully deflect into a flowpath of the fluid flowing through the drainage passage.

* * * * *